United States Patent [19]

Werdecker et al.

[11] Patent Number: 5,643,347
[45] Date of Patent: Jul. 1, 1997

[54] PROCESS FOR MANUFACTURE OF SILICA GRANULES

[75] Inventors: Waltraud Werdecker, Hanau; Rolf Gerhardt, Hammersbach; Hartwig Schaper, Aschaffenburg; Wolfgang Englisch, Kelkheim, all of Germany

[73] Assignee: Heraeus Quarzglas GmbH, Hanau, Germany

[21] Appl. No.: 459,408

[22] Filed: Jun. 2, 1995

[30] Foreign Application Priority Data

Jul. 11, 1994 [DE] Germany .................. 44 24 044.9

[51] Int. Cl.⁶ .................................................. C03B 19/10
[52] U.S. Cl. .................. 65/21.1; 65/21.4; 65/21.5; 65/17.3; 433/223
[58] Field of Search .................. 65/17.3, 21.1, 65/21.4, 21.5, 144; 264/117, 118; 433/223

[56] References Cited

U.S. PATENT DOCUMENTS

| | | | |
|---|---|---|---|
| Re. 25,564 | 4/1964 | Alford et al. | 65/21.4 X |
| 2,500,801 | 3/1950 | Church | 65/21.4 X |
| 3,321,414 | 5/1967 | Vieli | 65/21.4 X |
| 3,458,332 | 7/1969 | Alford et al. | 65/21.4 X |
| 4,042,361 | 8/1977 | Bihuniak | 65/18 |
| 4,105,426 | 8/1978 | Iler et al. | 65/17.3 |
| 4,200,445 | 4/1980 | Bihuniak et al. | 65/21.5 X |
| 4,952,530 | 8/1990 | Brosnan et al. | 501/39 |

FOREIGN PATENT DOCUMENTS

| | | |
|---|---|---|
| 1153507 | 9/1983 | Canada. |
| 335875 | 10/1989 | European Pat. Off. |
| 578553 | 1/1994 | European Pat. Off. |
| 291445 | 12/1985 | German Dem. Rep. |
| 2150346 | 5/1972 | Germany. |
| 3406185 | 9/1985 | Germany. |
| 62-202827 | 7/1987 | Japan. |

OTHER PUBLICATIONS

Ullmann's Encyclopedia of Industrial Chemistry Fifth edition.

*Primary Examiner*—Donald E. Czaja
*Assistant Examiner*—Sean Vincent
*Attorney, Agent, or Firm*—Felfe & Lynch

[57] ABSTRACT

To produce a free-flowing granulate which has a high bulk density and a defined particle size distribution, which generates little dust, is easy to handle, and is suitable as a starting material for quartz glass products, the mixing operation includes a first mixing phase, in which the materials to be mixed are subjected to a slow mixing action to form a coarse-grained mass, and a second mixing phase, in which the coarse-grained mass is converted to a fine-grained mass by a more intensive mixing action which grinds and compacts the grains. The content of silica powder in the materials to be mixed is adjusted at least during the second mixing phase to a value of at least 75 wt. %.

8 Claims, No Drawings

PROCESS FOR MANUFACTURE OF SILICA GRANULES

BACKGROUND OF THE INVENTION

The invention pertains to a process for the production of silica granulate by mixing silicic acid powder with a liquid.

Silica powders can be produced by means of gas-phase reactions such as by the hydrolysis of silicon halides or organic silicon compounds. They can also be produced by means of sol-gel processes. They are obtained in large amounts as a by-product of, for example, the production of synthetic quartz glass, but it is difficult to make profitable use of such powders. Although these silica powders are characterized by a very high degree of purity, they are very difficult to handle because of their high specific surface area and their low bulk density. Nor is there any easy way to melt them down by means of known processes into transparent quartz glass components with few if any bubbles.

To facilitate the handling of finely divided silica powders and to prepare them for the production of objects of quartz glass by means of conventional production methods, it is proposed in EP-B 335 875 that the BET surface area of the silica powder be reduced by mixing the silicic acid powder with water to form a crumbly mass; to dry the wetted powder; and then to grind, sieve, and temper the dried powder.

A similar process is also known from U.S. Pat. No. 4,042,361. In the process described in this publication for the workup of synthetic silica powder, the powder is mixed with water; the wetted powder is dried; and then the powder is tempered at a temperature of 1,000°–1,400° C. The granulate thus produced is suitable as a feed material for the production of quartz glass crucibles by the slip-casting method.

JP 62-202,827 proposes a method for producing a silica granulate in which silica powder with a particle diameter of less than 0.1 µm is mixed with a sodium-containing aqueous solution. This mixture is then dried, as a result of which agglomerates ranging in size from 50 to 500 µm are obtained. These agglomerates are then sintered and vitrified.

From DD 291 445, a process for the production of a granulate to be melted for quartz glass is known, according to which the starting material is lepidoid silicic acid, which is finely ground to a particle size of less than 60 µm and then dewatered at a temperature of 950°–1,200° C. After the addition of a 1% polyvinyl alcohol solution, the powder is finally converted by means of a sieve granulator into grains with sizes of less than 1 mm in diameter.

DE 34 06 185, a method for producing tablets of pyrogenically produced silicon dioxide particles. According to this method, a mixture of the pyrogenically produced oxide, a binder, water, and a lubricant is homogenized and pressed through a sieve. Then the granulate thus obtained is dried until it is solid enough to be press-molded. The granulate is pressed into molded articles, which are then sintered at 600°–850° C.

EP-A 578 553 describes a process for the production of a silica granulate by means of a sol-gel method. In the first step of this process, an aqueous suspension of silica powder is prepared, and the suspension is then gelled. After the gel has been dried, it is dispersed by microwaves. The suitable grain fraction is then sieved off.

The known processes require a large number of steps to arrive at a suitable grain size distribution, a sufficient degree of compaction, and satisfactory flow behavior of the granulate. The drying step in particular consumes a great deal of energy.

SUMMARY OF THE INVENTION

The present invention makes available a process for the production of a free-flowing granulate which has a high bulk density and a defined particle size distribution, which generates little dust and is easy to handle, and which is suitable as a starting material for the production of quartz glass products.

According to the invention the mixing operation comprises a first mixing phase, in which the material to be mixed is subjected to a slow mixing action to form a coarse-grained mass, and a second mixing phase, in which the coarse-grained mass is ground and compacted by means of a more intensive mixing action to obtain a fine-grained mass, the content of silica powder in the material being mixed being adjusted to at least 75 wt. % at least during the second mixing phase. The slow mixing makes it possible to produce a suspension with a large liquid component initially. The rheological properties of this suspension guarantee that the materials will be mixed thoroughly without excessive energy consumption, and additional silica powder can also be gradually incorporated into the suspension. The initial slow mixing action during the first mixing phase makes it possible gently to incorporate readily dust-generating silicac powder into the liquid or into the mixed material already present in the mixing container. Thus, a coarse-grained, crumbly mass is formed. By intensifying the mixing action during the second mixing phase, this coarse-grained mass is converted to a fine-grained mass by the grinding action exerted on the granulate and by the compaction of the individual grains. The grinding of the grains and the compaction of the newly formed fine grains come about as a result of the increased intensity of the impact and shear stresses being exerted on the material being mixed. These mechanical forces act to reduce the size of the grains only to a certain finite degree. After a certain mixing time has passed, the grains no longer continue to become smaller. The fine-grained mass therefore has an approximately uniform grain size and degree of compaction; the average grain size and the degree of compaction achieved depend essentially on the energy of the mixing action during the second mixing phase. The compaction of the mixed material caused by the accelerated mixing action is responsible for the high bulk density of the silica granulate. In addition, the division of the mixing operation into two defined mixing phases makes it possible to arrive at a high solids content in the mixed material. Because the content of silica powder is adjusted at least during the second mixing phase to 75 wt. % or more, an additional compaction of the fine-grained mass is achieved.

The silica granulates thus produced already have such a high bulk density and are already so free-flowing that they are easy to handle and use as such. A particular advantage of the process is that granulation can be carried out without the need for a binder. Binders frequently contain alkali metals, and these are harmful especially when the granulate is used to produce quartz glass components for high-temperature applications or when the granulate is used in applications in the field of semiconductor technology. Because of its low liquid content and high density, the silica granulates produced according to the invention can also be dried with relatively little expenditure of energy. They have good sintering properties and can be processed by means of the purification and sintering methods normally used for the raw materials for quartz glass to obtain high-quality quartz glass products.

Because of the free-flowing behavior of the material being mixed during the first mixing phase, doping agents introduced into the material such as pyrogenically produced aluminum oxide are distributed very quickly and uniformly.

An especially high degree of compaction can be achieved by increasing the mixing action from the first to the second mixing phase by at least 50%, preferably by 100% or more. It has been found advisable to intensify the mixing action in such a way that, on transition from the first to the second mixing phase, the liquid in the interior of the grains is forced to the surface of the grains. Once there, this liquid can be easily bound insofar as desired. It is advantageous for the duration of the second mixing phase to be selected in such a way that the phase is essentially over by the time the liquid has emerged from the silica grains.

The mixing action is preferably generated in a mixing container with a rotating whirling element, the peripheral velocity of which is adjusted to a value in the range of 15–30 m/s during the first mixing phase and to 30 m/s or more during the second. To obtain a high degree of compaction and a uniform grain size distribution, it has been found that subjecting the materials to intensive mixing and impact stress by the use of an intensive mixer in the second mixing phase yields good results.

Silica granulates with especially high bulk densities and especially low moisture contents are obtained when the content of silica powder in the first mixing phase is already at least 70%. This facilitates the subsequent compaction and the adjustment of the required solids content in the second mixing phase.

It has been found favorable to add silica powder to the mixed material immediately before or during the second mixing phase. By increasing the mixing motion in the second mixing step, a higher solid content can be incorporated and at the same time compaction of the granules can be achieved without interfering with the thorough mixing of the material on the first mixing step.

It is preferable to adopt a method in which the mixing operation also includes a third mixing phase, before or during which more silica powder is added to the mixed material, the intensity of the mixing action remaining essentially the same on transition from the second to the third phase. In this way, the previously obtained degree of compaction of the mixed material and the existing average grain size remain unchanged. The moisture which reached the surface of the grains during the preceding mixing phases can now be "dusted" by the addition of additional silica powder. This "dusting" has the advantageous result of preventing the moist granulate from agglomerating, and its free-flowing properties are improved. Simultaneously, the addition of silica powder results in a further increase in the solids content of the mixed material.

It has been found that adjusting the average grain size of the coarse-grained mass to a value in the range of 1–4 mm and that of the fine-grained mass to a value of less than 1 mm, preferably of 90–350 μm, gives good results. The grain size is adjusted by controlling the liquid content of mixed material and also, especially in the second mixing phase, by controlling the intensity of the mixing action.

For the production of free-flowing silica granulates with high bulk density, amorphous silica dust with an average particle size of less than 1 μm and with a BET surface area of more than 40 m$^2$/g has been found to be especially suitable as a starting material.

It is advantageous in terms of achieving a silica granulate with a high degree of chemical purity to use demineralized water with an electrical conductivity of less than 1 μS.

The surprising discovery has been made that the silica granulate according to the invention is an especially suitable starting material for the production of inorganic fillers such as those used in dental materials. Materials of this type are used, for example, as finely divided fillers in the organic plastics which play a role in dental technology. The silica granulate according to the invention generates little dust and is easy to handle because of its particle size and high compaction (about 10 times greater than that of the original silica powder). During compounding processes, it can be easily ground and uniformly distributed. To remove the residual moisture, it can be dried at temperatures of 80°–600° C. without undergoing any change in its structure or free-flowing behavior. To achieve a certain degree of consolidation, as desirable for applications as a filler in the dental area, for example, it is advantageous to subject the granulate to a heat treatment at a temperature of around 900° C. With the proper particle size distribution, the granulate is also suitable, however, for use as a catalyst support with high abrasion strength. For this purpose, it has been found that a heat treatment of the granulate at temperatures in the range of 1,000°–1,200° C. yields favorable results.

DETAILED EXAMPLE 14 kg of an amorphous silica dust with particles in the size range of 10–100 nm with a specific surface area of approximately 70 m$^2$/g was mixed together with 17 kg of demineralized water with an electrical conductivity of 0.1 μs in a high-speed mixer with a eccentrically mounted pinned-disk mixing element to produce an aqueous suspension. The high-speed mixer was operated at a speed of 750 rpm (corresponding to a peripheral velocity of 15.7 m/s). An additional 28 kg of amorphous silica dust was stirred into the suspension. After a mixing time of about 3 minutes, the mixed material assumed the form of a granular mass with an average grain diameter of less than 4 mm.

In a second mixing phase, an additional 11 kg of amorphous silicic acid dust was added to the mixed material, and the rotational speed of the pinned disk was doubled to 1,500 rpm (corresponding to a peripheral velocity of 31.4 m/s). As a result, the granular mass was subjected to both impact and shear stresses, which led to a grinding and compaction of the grains. At the same time, a portion of the water was forced to the surface of the grains. Water stopped emerging to the surface after about 20 minutes. To prevent the fine-grained mass thus produced from lumping together as a result of the expressed water, an additional 2 kg of silicic acid dust was added to the mixed material as the pinned disk continued to spin at a speed of 1,500 rpm in order uniformly to dust the surface of the granular material over a mixing period of about 15 seconds.

The fine-grained granulate thus produced was free-flowing, contained no binders, and had a defined particle size distribution, which was in the range of 90–350 μm. It had high strength and was therefore easy to handle. It had a residual moisture content of less than 24 wt. %. After removal of the residual moisture and possibly a partial consolidation at low temperatures, it is usable immediately as a "temporary" granulate for the production of inorganic fillers such as those used in dental materials or as a raw material with active sintering properties for the production of synthetic materials such as mullite. For this purpose, the granulate is ground immediately during the compounding process.

By means of a thermal treatment at temperatures of 1,000°–1,200° C., the granulate can be further consolidated without suffering any significant loss of specific surface area. A granulate of this type, which has a large pore volume, is suitable for the production of, for example, catalyst supports.

By means of a heat treatment at temperatures above about 1,350° C., the specific surface area of the granulate can be reduced to values of less than 1 m²/g. A granulate of this type without open pores is suitable as a feed material for the production of quartz glass.

We claim:

1. Process for the production of silica granules comprising providing a silica powder consisting of an amorphous silica dust having an average particle size of less than 1 μm and a BET surface area of at least 40 m²/g, in a first mixing phase, mixing said silica powder and a liquid at a first mixing rate until a mixture having an average silica grain size of 1–4 mm is obtained said silica content being at least 70 wt. %, and in a second mixing phase, mixing said mixture at a second mixing rate which is greater than said first mixing rate and adding silica powder until said mixture has an average grain size of less than 1 mm and a silica content of at least 75 wt. %.

2. Process as in claim 1 wherein said second mixing rate is at least 50% greater than said first mixing rate.

3. Process as in claim 1 wherein a transition is made from said first mixing rate to said second mixing rate in such a way that liquid present in said grains is forced out of said grains, and said second mixing phase continues until essentially all of said liquid is forced out of said grains.

4. Process as in main claim 1 wherein said mixing is performed in a mixing container with a rotating whirler element having a peripheral velocity, said peripheral velocity being 15–30 m/s in the first mixing phase and at least 30 m/s in the second mixing phase.

5. Process as in claim 1 further comprising adding silica powder to said mixture after said first mixing phase.

6. Process as in claim 1 further comprising adding silica powder to said mixture after said second mixing phase, said second mixing phase being followed by a third mixing phase wherein said mixture is mixed at said second mixing rate.

7. Process as in claim 1 wherein said mixture is mixed in said second mixing phase until said mixture has an average grain size of 90–350 μm.

8. Process as in claim 1 wherein said liquid consists of water having an electrical conductivity of less than 1 μs.

* * * * *

UNITED STATES PATENT AND TRADEMARK OFFICE
CERTIFICATE OF CORRECTION

PATENT NO. : 5,643,347
DATED : July 1, 1997
INVENTOR(S) : Werdecker et al.

It is certified that error appears in the above-identified patent and that said Letters Patent is hereby corrected as shown below:

Column 1,
Line 5, change "silicic acid" to -- silica --.
Line 22, change "silicic acid" to -- silica --.

Column 2,
Line 23, change "silicac" to -- silica --.

Column 5,
Line 13, following "obtained" add -- , --.

Signed and Sealed this

Eighteenth Day of January, 2005

JON W. DUDAS
*Director of the United States Patent and Trademark Office*